United States Patent
Bueno Ramirez et al.

(10) Patent No.: US 9,995,747 B2
(45) Date of Patent: Jun. 12, 2018

(54) SPECIFIC MONOCLONAL ANTIBODIES OF THE ANTIGEN M OF THE HUMAN METAPNEUMOVIRUS (HMPV) AND USE THEREOF IN A DIAGNOSTIC METHOD

(71) Applicant: PONTIFICIA UNIVERSIDAD CATOLICA DE CHILE, Santiago (CL)

(72) Inventors: Susan Marcela Bueno Ramirez, Santiago (CL); Alexis Mikes Kalergis Parra, Santiago (CL); Jorge Eugenio Mora Alarcon, Santiago (CL)

(73) Assignee: PONTIFICIA UNIVERSIDAD CATOLICA DE CHILE, Santiago (CL)

( * ) Notice: Subject to any disclaimer, the term of this patent is extended or adjusted under 35 U.S.C. 154(b) by 0 days. days.

(21) Appl. No.: 15/535,170

(22) PCT Filed: Feb. 2, 2015

(86) PCT No.: PCT/IB2015/050790
§ 371 (c)(1),
(2) Date: Jun. 12, 2017

(87) PCT Pub. No.: WO2016/092380
PCT Pub. Date: Jun. 16, 2016

(65) Prior Publication Data
US 2017/0343546 A1     Nov. 30, 2017

(30) Foreign Application Priority Data
Dec. 11, 2014   (CL) .................................. 2014-3373

(51) Int. Cl.
*G01N 33/569* (2006.01)
*C07K 16/10* (2006.01)

(52) U.S. Cl.
CPC ... *G01N 33/56983* (2013.01); *C07K 16/1027* (2013.01); *C07K 2317/14* (2013.01); *C07K 2317/56* (2013.01); *G01N 2333/115* (2013.01)

(58) Field of Classification Search
None
See application file for complete search history.

(56) References Cited

U.S. PATENT DOCUMENTS

2007/0248962 A1   10/2007   Gerna et al.

FOREIGN PATENT DOCUMENTS

WO   2004096993 A2   11/2004

OTHER PUBLICATIONS

N. Ishiguro, et al; Detection of antibodies against human Metapneumovirus by Western blot . . . ; Journal of Medical Virology; vol. 78; No. 8; Aug. 2006; pp. 1091-1095.
International Search Report dated Jun. 1, 2015 for PCT/IB2015/050790.
Written Opinion dated Jun. 1, 2015 for PCT/IB2015/050790 (Spanish—no English translation), English Translation Provided.

*Primary Examiner* — Nicole Kinsey White
(74) *Attorney, Agent, or Firm* — Lucas & Mercanti, LLP

(57) ABSTRACT

The invention relates to murine monoclonal antibodies corresponding to monoclonal antibodies secreted by cell lines of hybridomas denominated 3G8/C11 and 7G4/A12, and which react against the antigen M of hMPV. Said antibodies do not compete with each other for the binding site for binding to the antigen, nor do they impede the simultaneous binding thereof to the antigen. Said monoclonal antibodies can be used for tests for the detection, diagnosis and/or determination of infection by hMPV.

12 Claims, 6 Drawing Sheets

A

B

C

A

B

C

SPECIFIC MONOCLONAL ANTIBODIES OF THE ANTIGEN M OF THE HUMAN METAPNEUMOVIRUS (HMPV) AND USE THEREOF IN A DIAGNOSTIC METHOD

CROSS REFERENCE TO RELATED APPLICATION

This Application is a 371 of PCT/IB2015/050790 filed on Feb. 2, 2015, which claims priority of Chilean Application No. 2014-3373 filed Dec. 11, 2014, both of which are incorporated herein by reference.

FIELD OF THE INVENTION

The present invention relates to monoclonal antibodies or fragments thereof, that recognize the M protein of the respiratory virus Human Metapneumovirus (hMPV), useful for developing diagnostic methods for hMPV infection in humans.

BACKGROUND OF THE INVENTION

Human Metapneumovirus (hereinafter hMPV) is the etiological agent of a representative percentage of hospitalization and morbidity associated with acute respiratory diseases of the upper and lower respiratory tracts, especially in infants, elderly and immunocompromised individuals. This virus infection is associated with a wide range of pathologies, being bronchiolitis and pneumonia the conditions with a higher socio-economic impact. HMPV infection has been associated with gastroenteritis and keratoconjunctivitis. For example, Calvo et al. (2008) demonstrated over a period of 3 years that cumulative incidence of acute respiratory infections caused by respiratory viruses: respiratory syncytial virus (RSV), adenovirus (ADV) and hMPV accounted for 64.5% of hospital admissions of children younger than 2 years, being the incidence for each virus 35.4%, 19.3% and 9.8%, respectively. One interesting feature that hMPV shares with the other high-incidence respiratory viruses is the production of repeated infections throughout childhood, a phenomenon possibly associated with a failure to establish a protective immune response to the first infection during the first few months of life. To date, there are no studies about the specific economic impact of hMPV infection, however, the incidence of hospitalization for hMPV has been estimated to be ⅓ of the incidence of hospitalization for human respiratory syncytial virus (hRSV). Studies carried out in developed countries estimate that the individual cost of hRSV infection is over 3,000 euros ($1.86 million Chilean pesos) with an upper limit of up to 8,400 euros ($5.2 million Chilean pesos). The costs associated to individual hospitalization are approximate and based on a pathological process of similar features that requires hospitalization Although, hMPV and hRSV virus are grouped within the *Metapneumovirus* and *pneumovirus* genera, respectively, hMPV virus is classified in the Paramyxoviridae subfamily Pneumovirinae, the same family where hRSV is classified. hMPV genome comprises a non-segmented, single-stranded, negative-sense ribonucleic acid (ssRNA), so viral proteins are arranged in a 3' to 5' direction (relative to their sequence) as follows: N, P, M, F, M2 (ORF1 and ORF2), SH, G and L. Five of these proteins are responsible for packaging the genetic material and define the structure of the viral particle, corresponding to the nucleocapsid protein N and the matrix protein M, together with transmembrane glycoproteins F, G and SH, respectively. The other four proteins, M2-1, M2-2, P and L, are involved in viral replication and transcription. There are two subtypes of hMPV, classified as two antigenic groups A and B based on the sequence differences mainly found in the F and G proteins. Although these proteins have some degree of difference, there is a high identity compared to other proteins encoded by the viral genome.

HMPV detection is currently made using three techniques: RT-PCR, which amplified segments of the F and N genes directly from nasopharyngeal swabs samples, respiratory panel (direct immunofluorescence method routinely used in clinical laboratories, which allow simultaneous identification of different types of respiratory viruses) and in vitro culture in LLC-MK2 cells in order to detect a cytopathic effect. These techniques have a sensitivity not greater than 70% and both produce discordant results. One of the problems generated by low sensitivity and discordance between these techniques relates to the fact that respiratory infections negative for the respiratory panel are generally treated with antibiotics to avoid possible bacterial superinfections. Thus, false negative currently delivered by the available techniques are not receiving appropriate treatment and the patient is exposed to unnecessary antibiotic treatment, which further increases the possibility of generating antibiotic resistance in said patient.

Therefore, it is essential to have an effective and rapid diagnostic test for hMPV. Due to this problem, the monoclonal antibodies of the invention appear as a necessary alternative to fulfill this need, since they allow specific recognition of viral antigens in samples from patients infected with hMPV. Thus the present invention includes products such as monoclonal antibodies, and an alternative method that makes use thereof for accurate, effective and rapid detection and diagnosis in patients infected with hMPV with 100% specificity in clinical samples and capable to detect concentrations equivalent to 1.5 ng of the specific antigen by ELISA. This will allow clinicians to implement an early and appropriate treatment that could anticipate the disease course.

SUMMARY OF THE INVENTION

The present invention relates to monoclonal antibodies against Human Metapneumovirus (hMPV). Specifically, the present invention involves two murine monoclonal antibodies, corresponding to monoclonal antibodies secreted by hybridoma cell lines and designated as 3G8/C11 and 7G4/A12, which react against the antigen M of hMPV. These antibodies do not compete with each other for the antigen binding site or hindrance simultaneous binding to the same. Such monoclonal antibodies can be used in tests for the detection, diagnosis and/or determination of hMPV infection. These antibodies can be used simultaneously to increase the detection sensitivity in clinical samples having a small amount of antigen. For example, as shown in FIG. 6, antibodies from hybridoma 3G8/C11 are capable to efficiently capture the hMPV M-protein in clinical samples. These captured and immobilized proteins were subsequently detected by the antibodies generated by the hybridoma 7G4/A12, which were conjugated to an enzyme acting on a chromogenic substrate. This quality allows the combination of two antibodies with different labels to detect the same antigen in samples having a small amount of antigen.

The invention provides ex vivo or in vitro diagnostic methods for the detection of M viral antigen of hMPV, methods that use the monoclonal antibodies produced and secreted by hybridomas 3G8/C11 and 7G4/A12 in tests such as ELISA, fluorescence microscopy and immunoblot. Samples to be analyzed can be: in vitro hMPV-infected cells, nasal secretions, nasal washes, pharyngeal secretions and/or bronchial secretions or washings, and others. The invention provides a method of detecting hMPV in biological samples and cell cultures, using monoclonal antibodies produced and/or secreted by the above hybridoma cell lines coupled on any solid support, such as nitrocellulose, nylon membrane, magnetic beads, fluorescent beads, or other support; or coupled to any other molecule, such as enzymes, proteins, fluorophores, radioactive isotopes or any other chemical compound. The invention can be used in hMPV detection kits comprising the antibodies produced by said hybridomas. The scope of the present invention further encompass any type of chemically bonded molecule or substrate, such as labels, fluorophores, biotin, radioisotopes, metals, enzymes and/or any chemical element coupled to the monoclonal antibodies secreted by hybridomas 3G8/C11 and 7G4/A12, wherein said chemically bonded molecule or substrate allows for the visualization or detection of the antibody. Thus, the invention also provides antibodies that specifically recognize the M protein coupled to different molecules or substrates or markers of the antibody, as part of the detection, analysis and/or diagnostic method in biological samples.

DETAILED DESCRIPTION OF THE INVENTION

Figure 1:
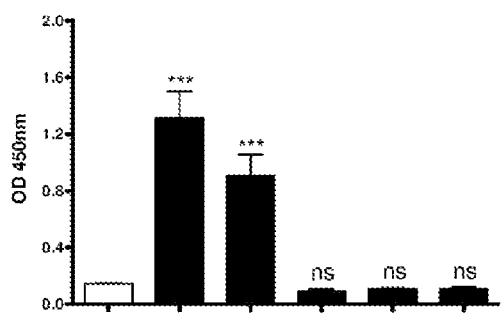
FIG. 1: Detection of hMPV M-Protein by monoclonal antibodies produced by hybridomas 3G8/C11 and 7G4/A12, by indirect ELISA test protein. The plate was activated with 50 ng of purified recombinant hMPV M-protein or $1\times10^6$ PFU of hMPV. Other wells were activated with $1\times10^6$ PFU of Respiratory Syncytial Virus (RSV) or 50 ng of BSA protein as negative controls; control wells without antigen but with primary antibody, HRP-conjugated anti-mouse IgG (unactivated), and wells without antigen or primary antibody but only with anti-mouse IgG (HRP) antibody were also included. Subsequently, wells were incubated with anti-M antibodies from hybridoma 3G8/C11, in an amount of 170 ng (A); hybridoma 7G4/A12 in an amount of 170 ng (B); and the commercial Anti-Human Metapneumovirus 75.1 Antibody, clone 1B7, catalog number MAB8510 (EMD Milliporeused in an amount of 680 ng (C). The data shown in the graph indicate the absorbance detected at 450 nm, emitted by conversion of Tetramethylbenzidine substrate to a colored compound, catalyzed by the Horseradish peroxidase (HRP) enzyme present on a secondary anti-mouse IgG bound specifically to the antibodies secreted by hybridomas 3G8/C11, 7G4/A12 and MAB8510 from Millipore. Values are the average +/− standard deviation of the absorbance emitted by each sample in at least two independent experiments. P<0.01 and *P<0.0001 by one-way ANOVA test relative to the negative control and verified by Dunnett's multiple comparison; ns, no significant difference compared to the negative control.
Figure 1:
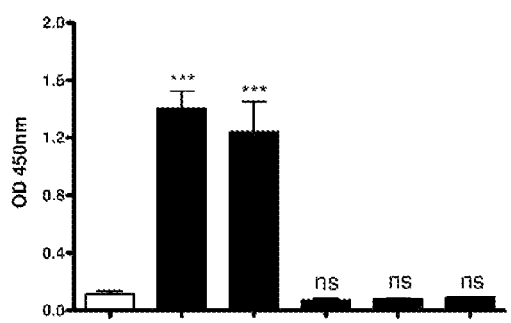
Figure 1:
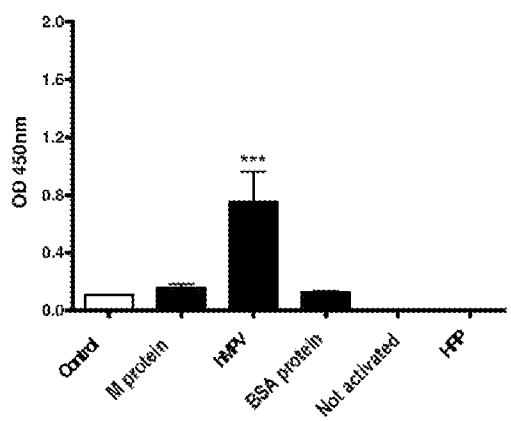

The present invention relates to two isotype IgG2a monoclonal antibodies or fragments thereof, which specifically recognize the M-protein (also herein referred as anti-M antibodies) of human Metapneumovirus (hMPV).

A monoclonal antibody is a type of homogeneous antibody characterized by specifically recognizing a single antigen. They are produced by a single hybrid cell (hybridoma), which is the product of the fusion of a B lymphocyte clone and a tumor plasma cell. The property of binding specifically and with high affinity to an antigen has promoted the development of monoclonal antibodies as a tool of great utility for the detection of molecules that generate a great scientific and clinical interest and which are of industrial use. At present, monoclonal antibodies are widely used, both in basic and applied research, due to their specificity and reproducibility, which allows a better support for research. However, the biomedical area is where monoclonal antibodies have had enormous practical applications, either for diagnosis and treatment of multiple infectious diseases, and as therapy for other pathologies. While monoclonal antibodies are used in all types of detection and diagnosis techniques, the best results have been obtained in designing in vitro diagnostic kits. For this, there are currently available several rapid detection kits, such as pregnancy tests, which is based on the determination of human chorionic gonadotropin (hCG) levels in urine using anti-hCG antibody. In addition, monoclonal antibodies for therapeutic use have become highly relevant. Currently, there are therapeutic treatments for various pathologies using commercial monoclonal antibodies such as Alemtuzumad, Gemtuzumab ozogamicin, Rituximab, Trastumab, among others.

The inventors of the present invention have developed two monoclonal antibodies that specifically recognize the M protein of hMPV. As indicated above, these antibodies are produced by hybridomas 3G8/C11 and 7G4/A12. The variable region amino acid sequences of both chains of the antibody produced by hybridoma 3G8/C11 are set forth in SEQ ID NO: 1 for the heavy chain and SEQ ID NO: 2 for the light chain. The nucleotide sequences encoding the same are set forth in SEQ ID NO: 3 and SEQ ID NO: 4, respectively. Similarly, the variable region amino acid sequences of both chains of the antibody produced by hybridoma 7G4/A12 are set forth in SEQ ID NO: 5 for the heavy chain and SEQ ID NO: 6 for the light chain. The nucleotide sequences encoding the same are set forth in SEQ ID NO: 7 and SEQ ID NO: 8, respectively.

A skilled artisan starting from these variable sequences could construct chimeric antibodies comprising the same, including either only one variable region or combining them using all possible combinations. All such embodiments are within the scope of the present invention. That is, the present invention includes antibodies comprising at least one of the sequences SEQ ID NO: 1, SEQ ID NO: 2, SEQ ID NO: 5 and SEQ ID NO: 6 and similar sequences with up to 90%, 95% or 99% homology or identity to any of said amino acid sequences. As well as the nucleotide sequences comprising at least one of the sequences SEQ ID NO: 3, SEQ ID NO: 4, SEQ ID NO: 7 and SEQ ID NO: 8, and their reverse complementary and similar sequences with up to 80%, 85%, 90%, 95% and 99% homology or identity to any of said nucleotide sequences. The highest degree of homology considered in the nucleotide sequences is based on the degeneracy of the genetic code. Thus, the present invention also includes a set of nucleotide sequences encoding a monoclonal antibody or fragment thereof, which specifically recognizes the M-protein of hMPV.

Figure 4:
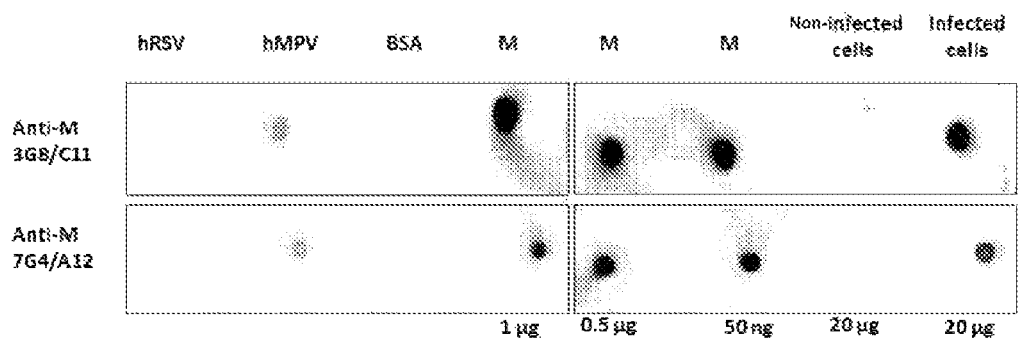
FIG. 4. Confirmation of specificity of monoclonal antibodies secreted by hybridomas 3G8/C11 and 7G4/A12, by dot blot. The anti-hMPV M antibodies produced by hybridomas 3G8/C11 or 7G4/A12 were incubated for 1 hour with a nitrocellulose membrane containing the following immobilized samples (as dots): RSV ($1\times10^6$ PFU), hMPV ($1\times10^6$ PFU), BSA (1 µg), hMPV M-protein (1 µg, 500 ng and 50 ng) protein, and 20 µg of non-infected and hMPV-infected LLC-MK2 cell extract. After incubation, the membrane was washed and incubated for 1 hour with an anti-mouse IgG secondary antibody conjugated to the HRP protein. After incubation, binding of monoclonal antibodies to the antigen was observed by capturing the chemiluminescence produced by the commercial substrate "enhanced chemiluminescence Western blot detection system" (ECL, Amersham, Uppsala, Sweden) catalysis. It is observed that the antibodies produced by hybridomas 3G8/C11 or 7G4/A12 bind only to the dots where the hMPV M-protein, hMPV virus and cells infected with hMPV are present, confirming the specificity of these antibodies.

As shown in FIGS. 1 and 4, these antibodies do not react with other proteins or molecules present in related viruses or samples from patients with other respiratory infections associated virus. This significantly lowers the possibility of false negatives when used in diagnostic methods.

Examples are given below to demonstrate the different applications of monoclonal antibodies of the invention.

Example 1: Determination of the Nucleotide Sequence Encoding Light (VL) and Heavy (VII) Chains of the Variable Region of Anti-hMPV M Antibody Secreted from Hybridoma 3G8/C11

Hybridoma 3G8/C11 was grown in DMEM-high glucose culture medium supplemented with 3.7 g/L Sodium Bicarbonate and 10% fetal bovine serum, at 37° C. with 10% $CO_2$ up to a cell density of 700,000 cells/ml. A total RNA of 3.5 $\times 10^6$ cells was obtained by performing a treatment with the compound Trizol (Invitrogen). 0.5 µg of RNA were used to generate cDNA by reverse transcription reaction using Impron II kit (Promega). The variable region of the genes encoding immunoglobulin kappa and lambda chains was amplified by PCR. To carry on this, universal primers from Novagen Ig-Primer Set kit (Catalog No. 69831-3) were used according to the manufacturer's instructions. Light chain variable region was amplified with primers MuIgκVL5'-B: 5' GGGAATTCATGGAGACAGACACACTCCTGCTAT3' (SEQ ID NO: 9) y MuIgκVL5'-C: 5'ACTAGTCGACATG-GAGWCAGACACACTSCTGYTATGGGT3' (SEQ ID NO: 10) and heavy chain variable region was amplified with primers MuIgVH5'-A: 5' GGGAATTCATGRASTTSKG-GYTMARCTKGRTTT3' (SEQ ID NO: 11) and MuIgVH5'-F: 5'ACTAGTCGACATGAACTTYGGGYTSAGMTT-GRTTT3' (SEQ ID NO: 12). PCR products were cloned into the cloning vector pTOPO-TA (Invitrogen) according to the manufacturer's instructions and sequenced by the sequencing service of the Pontificia Universidad Católica de Chile in an ABI prism 3130×1 sequencer (Applied Biosystem). The deduced amino acid sequence was obtained using the Vector NTI bioinformatic program (Invitrogen).

Example 2: Determination of the Nucleotide Sequence Encoding Variable Light (VL) and Heavy (VII) Chains of Anti-hMPV M Antibody Secreted from Hybridoma 7G4/A12

Hybridoma 7GA/A12 was grown in DMEM-high glucose culture medium supplemented with 3, 7 g/L Sodium Bicarbonate and 10% fetal bovine serum, at 37° C. with 10% $CO_2$ up to a cell density of 700,000 cells/ml. A total RNA of 3.5 $\times 10^6$ cells was obtained with Trizol (Invitrogen). 0.5 µg of RNA were used to generate cDNA by reverse transcription reaction using Impron II kit (Promega). The variable region of the genes encoding immunoglobulin kappa and lambda chains was amplified by PCR. To carry on this, universal primers from Novagen Ig-Primer Set kit (Catalog No. 69831-3) were used according to the manufacturer's instructions. Light chain variable region was amplified with primers MuIgκVL5'-B: 5'GGGAATTCATGGAGACAGA-CACACTCCTGCTAT3' (SEQ ID NO: 9) y MuIgκVL5'-C: 5'ACTAGTCGACATGGAGWCAGACACACTSCT-GYTATGGGT3' (SEQ ID NO: 10) and heavy chain variable region was amplified with primers MuIgVH5'-A: 5'GGGGAATTCATGRASTTSKGGYTMARCTKGRTTT3' (SEQ ID NO: 11) and MuIgVH5'-F: 5'ACTAGTCGACAT-GAACTTYGGGYTSAGMTTGRTTT3' (SEQ ID NO: 12). PCR products were cloned into the cloning vector pTOPO-TA (Invitrogen) according to the manufacturer's instructions and sequenced by the sequencing service of the Pontificia Universidad Católica de Chile in an ABI prism 3130×1 sequencer (Applied Biosystem). The deduced amino acid sequence was obtained using the Vector NTI bioinformatic program (Invitrogen).

Example 3: Test for hMPV Antigen Detection, Determination of Monoclonal Anti-hMPV M Antibodies Specificity for Purified hMPV Antigens by Indirect ELISA Test The object of this test is show the specificity of antibodies produced by hybridomas 3G8/C11 and 7G4/A12 for the hMPV M-protein. Antigen detection was performed by indirect ELISA, where the ELISA plate was activated with 50 ng of purified antigen for 1 hour at 37° C. Similarly, the plate was activated with $1 \times 10^6$ plaque forming units (PFU) of hMPV. Respiratory Syncytial Virus (RSV) under the same conditions of hMPV incubation, and 50 ng BSA protein in a separate well were included as negative controls. Subsequently, the plate was washed two times with phosphate buffered saline (PBS)/0.05% Tween. The plate was then blocked for 2 hours at 37° C. with PBS/10% FBS. Washings were subsequently repeated and then each one of the antibodies (3G8/C11 and 7G4/A12) was incubated at a final concentration of 3.4 µg/ml, diluted in PBS/10% FBS for 1 hour at room temperature (each antibody in a separate plate). A control test was made in a different plate under the same conditions using a commercial monoclonal antibody recognizing the hMPV M-protein (Anti-human Metapneumovirus 75.1 antibody, clone 1B7, catalog number MAB8510, EMD Millipore) at concentration of 13.6 µg/ml. After the incubation time, washes were repeated and an anti-IgG mouse secondary antibody labeled with horseradish peroxidase enzyme (Horseradish peroxidase, HRP) at 1:2000 dilution (25 ng per well) in PBS/10% FBS was added to each of the wells for 1 hour at room temperature. Finally, washes were performed and it was developed with 50 µl of citrate buffer/Tetramethylbenzidine (TMB, 3-3'-5-5'tetramethyl-benzidine, 1 mg/ml, Becton Dickinson). 50 µl of 2N $H_2SO_4$ was added to stop the reaction and the result was read in an ELISA plate reader at 450 nm. To evaluate if the reaction of the secondary antibody was specific to recognize the primary antibody and if the obtained signal is not caused by nonspecific binding of the secondary antibody to the viral antigen, controls using only secondary antibody with no primary antibody and no sample were made (non-activated well). Another control to evaluate if the reaction of the primary antibody is specific for the antigen was the use of the antibodies on an ELISA plate not activated with the antigen (well with no antigen) or using the antibody on an ELISA plate having 50 ng of BSA protein or a different virus (RSV). Results show that the monoclonal antibodies of the invention are capable of recognize 50 ng of purified antigen specifically since they do not recognize BSA protein or proteins from other associated virus (FIGS. 1A and 1B). Furthermore, it was observed that the commercial antibody (FIG. 1C) used in the test as a control, even being specific for detecting the virus, was not efficient for detecting the purified recombinant hMPV M-protein in our laboratory.

Example 4: Test for Determination of the Sensitivity of the Monoclonal Antibodies for Viral Antigen Detection The test was performed for the determination of the highest virus and protein dilution detectable by monoclonal anti-hMPV M antibodies from hybridomas 3G8/C11 and 7G4/A12, this was made by indirect ELISA. For achieve this, the same technique described in Example 3 was used. The plate was activated with eleven serial dilutions 1:2 of hMPV M-protein, starting with 50 ng of purified antigen. For the virus, the plate was activated with 1:2 serial dilutions starting from $1 \times 10^5$ PFU of virus. The anti-M antibodies 3G8/C11 or 7G4/A12 were used at a concentration of 3.4 µg/ml (170 ng/well) diluted in PBS/10% FBS. Subsequently the detection anti-mouse IgG antibody was added at a dilution of 1:2000 (25 ng/well). The results showed that the anti-M antibody 3G8/C11 is capable to recognize up to 190 picograms (pg) of the hMPV M-protein. The anti-M antibody from hybridoma 7G4/A12, was more sensitive and detected up to 90 pg of the hMPV M-protein (FIG. 2A).

Figure 2:
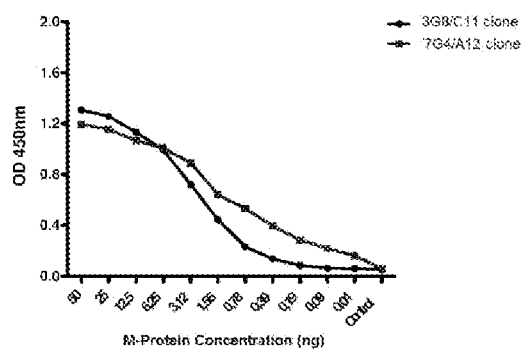
FIG. 2: Determination of sensitivity of monoclonal antibodies produced by hybridomas 3G8/C11 and 7G4/A12 for detection of hMPV M-protein. ELISA plates were activated with 1:2 serial dilutions, starting with 50 ng M-Protein and ending with 0.04 ng (A); or 1:2 serial dilutions, starting from an inoculum of $1\times10^5$ PFU hMPV up to a 1:5120 dilution (B); and 1:2 serial dilutions, starting from an inoculum of $1\times10^6$ PFU hMPV up to a 1:64 dilution (C). Non-activated wells were included as negative control. The data shown in the graph indicate the absorbance detected at 450 nm, emitted by conversion of Tetramethylbenzidine substrate to a colored compound, catalyzed by the Horseradish peroxidase (HRP) enzyme present on the anti-M antibodies from hybridomas 3G8/C11 and 7G4/A12 in amount of 170 ng (A and B). The commercial anti-hMPV M antibody was used at a higher amount (680 ng) (C). The values are the average absorbance emitted by each sample in at least two independent experiments.
Figure 2:
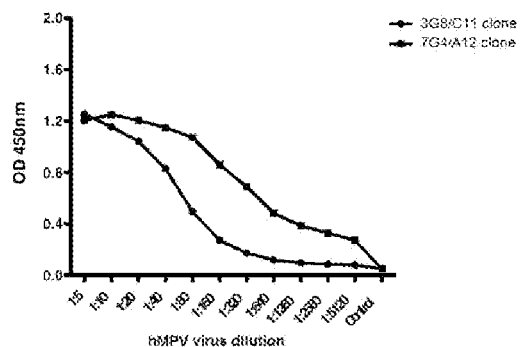
Figure 2:
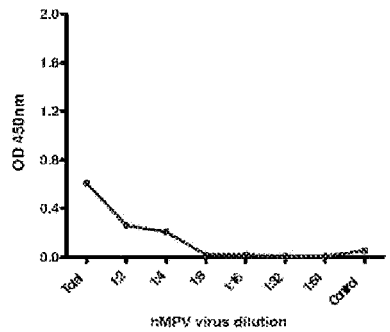

As for the sensitivity of the antibodies represented by its ability to detect hMPV at high dilution, it was seen that anti-M antibody from hybridoma 3G8/C11 can detect virus dilutions up to 1 in 60, while the antibody from hybridoma 7G4/A12 is capable of detecting the protein in the virus at a dilution of 1:2560, which is equivalent to approximately 390 viral particles (FIG. 2B).

The ability of Millipore commercial antibody to detect the virus was evaluated, 1:2 dilutions were made starting from $1 \times 10^6$ PFU. It was found that the antibody is capable of detecting $1 \times 10^6$ PFU and two more dilutions, i.e., up to a dilution of 1:4 of total virus (FIG. 2C).

Controls that could rule out non-specific reactions of both antibodies were included in all tests, they contained all test components excluding the sample (hMPV M-protein or virus).

Figure 3:
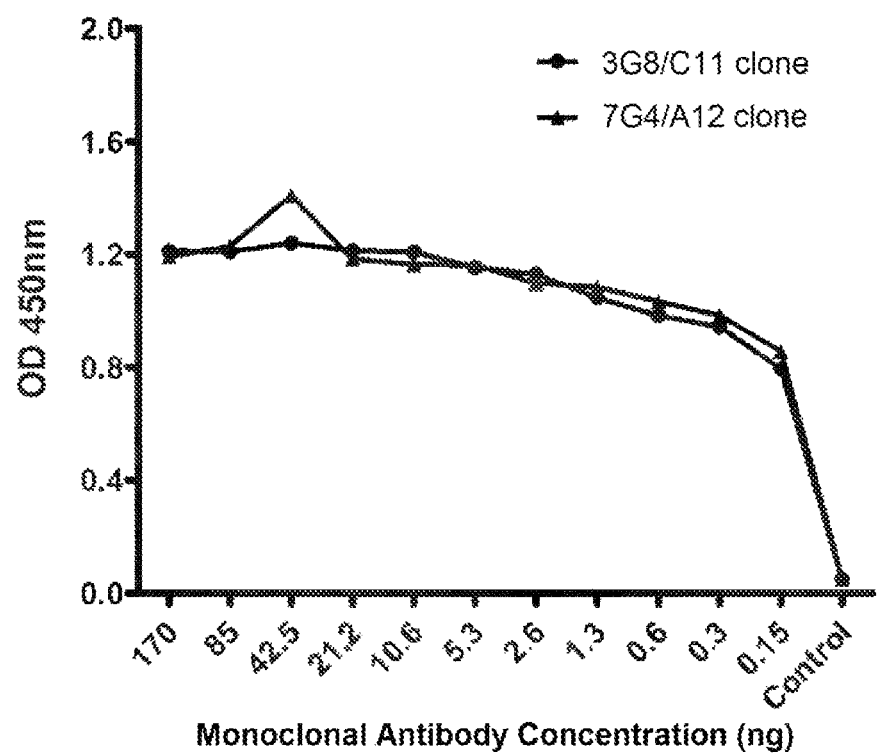
FIG. 3: Serial dilution test of monoclonal anti-hMPV M antibody produced by hybridomas 3G8/C11 and 7G4/A12, for detection of hMPV purified antigens. ELISA plates were activated with 50 ng of recombinant hMPV M-protein and the antigen was detected with 1:2 serial dilutions of 3G8/C11 or 7G4/A12 anti-M antibodies, starting from a 3.4 µg/ml (170 ng) concentration. All data are expressed as the average value of absorbance emitted at 450 nm of each sample in duplicate in at least two independent experiments.

Example 5: Test for Determination of Efficiency of Monoclonal Antibody to Detect Viral Antigens The test was performed for determination of the highest dilution of monoclonal anti-hMPV M antibodies from hybridomas 3G8/C11 and 7G4/A12, which allows detection of viral antigen. To achieve this, the same ELISA technique described in Example 4 was used. The plate was activated with 50 ng of purified antigen and the anti-M antibodies 3G8/C11 or 7G4/A12 were used at 1:2 dilutions, starting from the working concentration (3.4 µg/ml) up to 11 dilution in PBS/10% FBS. FIG. 3 shows that the anti-M 3G8/C11 and 7G4/A12 are capable to detect the hMPV M-protein at all dilutions used in the test.

The negative control included in this test was one well containing no sample (M protein), it was blocked with PBS/10% FBS, primary antibody (anti-M 3G8/C11 or anti-M 7G4/A12) was not added and contains only HRP-conjugated anti-mouse IgG.

Example 6: Specificity Test of Monoclonal Anti-hMPV M Antibodies for Purified hMPV Antigens, by Dot-Blot Test This test is made to confirm the specificity of the antibodies produced by hybridomas 3G8/C11 and 7G4/A12 for hMPV M-protein, using immunoblot methodology. Antigen detection was performed by dot-blot technique, where a nitrocellulose membrane is used as solid support for immobilizing the antigen in a drop of suspension. To achieve this, 20 μl was deposited on the nitrocellulose membrane, each containing: $1\times10^6$ PFU of RSV, $1\times10^6$ PFU of hMPV, purified hMPV M-protein (1 μg, 500 ng and 50 ng), 20 μg of hMPV-infected LLC-MK2 cell extract and 20 μg of non-infected LLC-MK2 cell extract. 500 ng BSA contained in 20 μl were applied as negative control. Solutions applied onto the membrane were allowed to air dry for 15 minutes. Subsequently, the membrane was blocked with 5% BSA in PBS containing 0.05% Tween-20 for 1 h at 25° C. Membranes were incubated with 3.4 μg/ml of monoclonal anti-M antibody from hybridoma 3G8/C11 or hybridoma 7G4/A12 in blocking solution for 1 h at 25° C. The excess antibody not bound to the antigen was removed by three washes with PBS-0.05% Tween-20 at 25° C. The antibodies bound to the antigen were detected using an HRP-conjugated anti-mouse IgG antibody (Invitrogen, Life Technologies #62-6520). This was incubated for 1 h in blocking solution at 25° C. to subsequently remove the excess of unbound antibody by three washes with PBS-0.05% Tween-20 at 25° C. Binding of the monoclonal antibodies to the antigen was observed by capturing the chemiluminescence produced by the commercial substrate "enhanced chemiluminescence Western blot detection system" (ECL, Amersham, Uppsala, Sweden) catalysis, mediated by HRP enzyme bound to anti-mouse IgG. Chemiluminescence capture was performed with the MyECL photodocumentation system (Thermo Fisher). As seen in FIG. 4, the antibodies from hybridomas 3G8/C11 and 7G4/A12 only bind to "dots" containing hMPV or M protein, and do not bind unspecifically to "dots" containing unrelated proteins, other viruses or non-infected cells.

Figure 5:
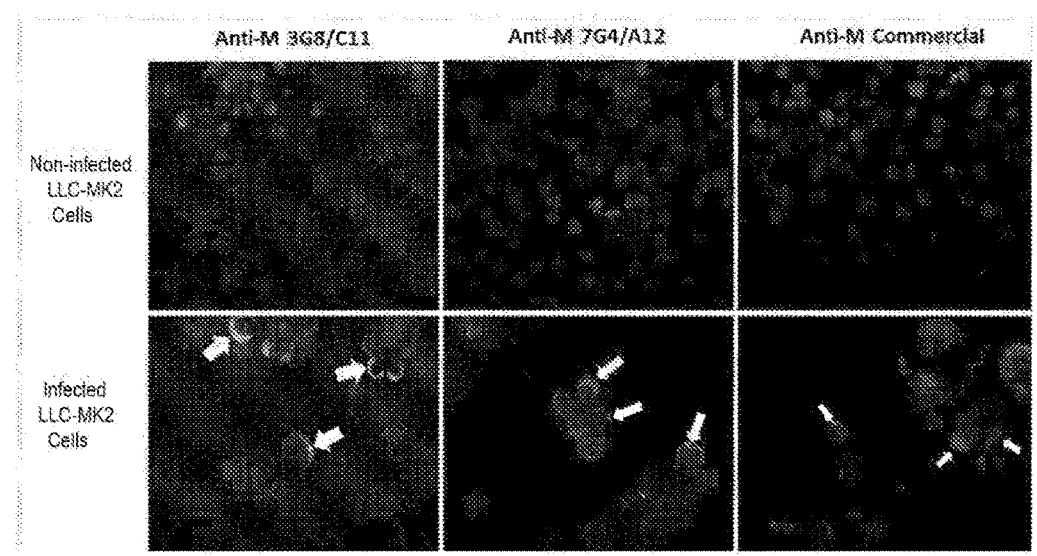
FIG. 5. Detection of hMPV M-protein by immunofluorescence in hMPV-infected LLC-MK2 cells. LLC-MK2 cells were grown in vitro until reaching confluence (70-90%), to be infected with hMPV for 48 hours. They were then fixed with paraformaldehyde and prepared for indirect immunofluorescence. A monoclonal primary antibody derived from hybridoma 3G8/C11, hybridoma 7G4/A12 or commercial antibody MAB8510 from Millipore was used. A commercial anti-mouse IgG antibody conjugated to the fluorophore Alexa Fluor 488 emitting fluorescence at 519 nm (signal intense) was used as a secondary antibody. The cell nuclei were stained with fluorophore TOPRO-3 iodide emitting fluorescence at 661 nm (filled circles). A strong reactivity in the cytoplasm (white arrows) is observed only in infected cells when any of the three primary antibodies are used.

Example 7: Detection of hMPV Infection in LLC-MK2 Cells by Immunofluorescence Using Monoclonal Anti-M hMPV Antibodies This test was performed to broaden the spectrum of techniques that detect hMPV infection using the disclosed invention. A fluorescence microscopy test was carried out, wherein non-infected and hMPV-infected LLC-MK2 cells were incubated with monoclonal anti-hMPV M antibodies derived from hybridomas 3G8/C11 or 7G4/A12. The protocol used was as follows: the cells were fixed with 4% paraformaldehyde diluted in PBS, for 10 minutes at 25° C. Cells were then washed with PBS and permeabilized with 0.2% saponin diluted in PBS/10% FBS by 30 minutes at 25° C. Monoclonal antibodies derived from hybridomas 3G8/C11 or 7G4/A12 were added at a concentration of 3.4 μg/ml, diluted in PBS/10% FBS for 1 hour at 25° C. Two washes were then performed with PBS and the anti-mouse IgG secondary antibody conjugated to the fluorophore Alexa Fluor 488 (Life Technologies) was added at a dilution of 1 in 200 in PBS/10% FBS for 1 hour at 25° C. in the dark. Washes were repeated and the nuclei was stained with TOPRO-3 iodide 642/661 (Invitrogen, #-T3605) at a 1:5000 dilution for 15 minutes at 25° C. in the dark. Finally, it was washed with PBS and coverslip assembly was made in an epifluorescence microscope for further observation. The obtained results show that the antibodies of the invention are also useful to recognize specifically infected cells by immunofluorescence, without binding nonspecifically to non-infected cells (FIG. 5).

Figure 6:
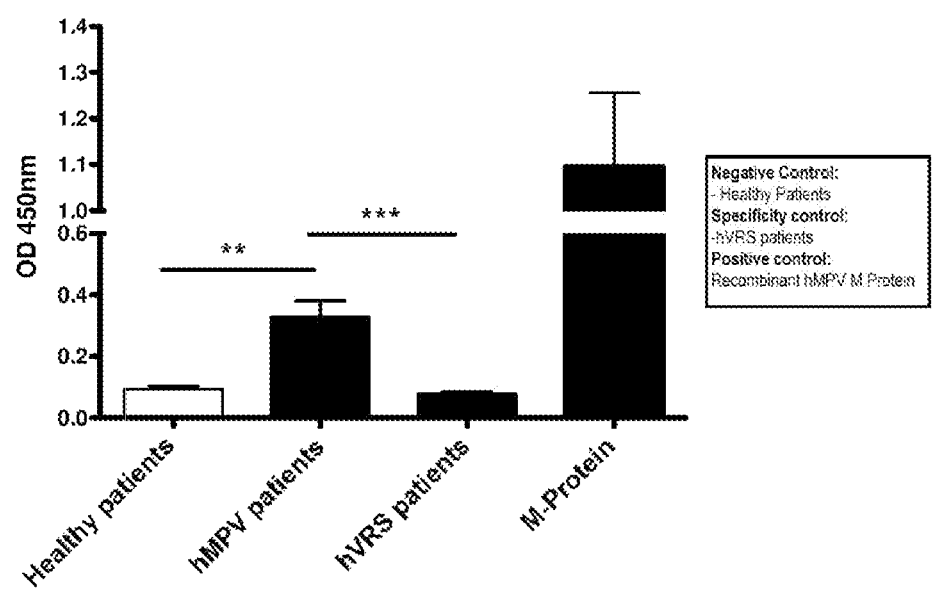
FIG. 6: Detection of hMPV in clinical samples by sandwich ELISA, using the combination of the monoclonal antibodies secreted by the hybridomas 3G8/C11 and 7G4/A12. ELISA plates were activated with 170 ng of antibody secreted by the hybridoma 3G8/C11 working as capture antibody. The wells activated with the capture antibody were incubated with 50 µl of nasopharyngeal swab (NPS) samples of patients with viral respiratory symptoms. 10 samples from healthy patients were analyzed as negative controls. 20 samples of hMPV positive patients were used and 20 samples patients positive to Respiratory Syncytial Virus were included as a control of specificity. Wells added with purified hMPV-M protein were included as positive control. To detect the protein captured by the 3G8/C11 antibody, antibodies produced by hybridoma 7G4/A12 conjugated to the Horseradish Peroxidase enzyme in a 1:2000 dilution (75 ng per well) were used. The data shown are the average +/− standard deviation of the absorbance emitted at 450 nm for each sample (P<0.01 *P<0.0001 and ns: no significant difference, using the one-way ANOVA test compared with RSV positive patients or healthy patients).

Example 8: Clinical Diagnosis of Samples of hMPV Infected Patients, Using Monoclonal Anti-hMPV M Antibodies from Hybridomas 3G8/C11 and 7G4/A12, by Sandwich or Capture ELISA Due to the low availability and concentration of viral proteins in the clinical samples obtained from nasopharyngeal swabs, it was necessary to modify the detection method and use capture or sandwich ELISA, using the anti-M antibody from hybridoma 3G8/C11 as capture antibody and the HRP-conjugated anti-M 7G4/A12 clone as detection antibody. For the test, ELISA plate wells were activated with 3.4 μg/ml (170 ng/well) of anti-M antibody from hybridoma 3G8/C11 diluted in PBS, for 1 hour at 37° C. Two washes with PBS-0.05% Tween 20 were made and the plate was then blocked with 200 μl PBS/10% FBS for 2 hours at 37° C. It was washed again and incubated at 4° C. overnight, each well with 50 μl nasopharyngeal aspirates from hMPV-positive patients according to the method of diagnosis "D³ Ultra DFA Respiratory Virus Screening and ID Kit DHI (Diagnostics Hibryds) USA", routinely called as "viral panel", and which were treated as described below*. As controls were included: 1) control of specificity (50 μl sample of patients diagnosed with RSV by viral panel), 2) positive control (50 ng of recombinant hMPV M-protein) and 3) negative control corresponding to healthy patient samples (negative for virus by viral panel). Washes were made the next day and each well was incubated for 1 hour at room temperature with 50 μl of HRP-conjugated anti-M antibody from hybridoma 7G4/A12. The plate was washed 2 more times and developed with 50 μl TMB solution, it was incubated for 10 to 15 minutes in the dark. The reaction was stopped with 50 μl 2N $H_2SO_4$. Plates were read in an Epoch ELISA reader, certified for clinical diagnosis. The results for this test are shown in FIG. 6, where it can be seen that the sandwich ELISA technique using the antibody from hybridoma 3G8/C11 as the capture antibody and the antibody from hybridoma 7G4/A12-HRP as detection antibody, allowed antigen detection in samples from hMPV-infected patients, which were previously confirmed positive by direct immunofluorescence in a certified clinical laboratory using the viral panel. The number of patients included in the trial was 20, 18 of which were detected as positive by ELISA with an optical density (OD) above 0.1. This test also demonstrates the versatility of the antibodies from hybridomas 3G8/C11 and 7G4/A12, since they are capable of simultaneously bind the antigen without competing or interfering with each other, allowing the capture and subsequent detection of M-protein in patient samples.

*Treatment of clinical samples. The samples used for testing were obtained from nasopharyngeal swabs contained in universal transport medium. Samples were centrifuged at 2000 rpm for 10 minutes at 4° C. Subsequently the supernatant (SN1) was separated from the pellet; the latter was incubated with 100 μl RIPA Buffer (50 mM Tris-HCl pH 8.0, 150 mM NaCl, 1% NP-40, 0.5% sodium deoxycholate, 0.1% SDS and a cocktail of protease inhibitors) for 15 minutes at 4° C., vortexing every 5 minutes. Then it was centrifuged at 2000 rpm for 10 minutes at 4° C. Finally, the obtained supernatant (SN2) was collected and mixed with SN1.

Examples described herein demonstrate the specificity, efficiency, sensitivity and versatility of these monoclonal anti-hMPV M antibodies secreted by cell lines of hybridomas 3G8/C11 and 3G8/C11. The examples presented herein are a demonstration of some of the uses of the monoclonal anti-hMPV M antibodies, but in no case are limiting the scope of the present invention.

The invention claimed is:

1. A monoclonal antibody or a fragment thereof which binds to the M-protein of respiratory virus human Metapneumovirus (hMPV), wherein the monoclonal antibody comprises a heavy chain variable region having SEQ ID NO: 1 or SEQ ID NO: 5 and a light chain variable region having SEQ ID NO: 2 or SEQ ID NO: 6.

2. The monoclonal antibody or a fragment thereof which binds to the M-protein of respiratory virus human Metapneumovirus (hMPV) according to claim 1, wherein the antibody or fragment is further bound to a marker selected from the group consisting of fluorophores, biotin, radioisotopes, metals and enzymes.

3. A set of nucleotide sequences encoding a monoclonal antibody or a fragment thereof that binds to the M-protein of respiratory virus human Metapneumovirus (hMPV) according to claim 1, wherein the set comprises a nucleotide sequence with SEQ ID NO: 3, or SEQ ID NO: 7 or a reverse complementary thereof, which encodes the antibody heavy chain variable region and comprises a nucleotide sequence having SEQ ID NO: 4 or SEQ ID NO: 8 or a reverse complementary thereof, which encodes the antibody light chain variable region.

4. An vitro and/or ex vivo diagnostic method for hMPV infection in a biological sample, wherein the method comprises contacting the biological sample with the monoclonal antibody against hMPV or an antigen binding fragment thereof according to claim 1 and detecting antibody binding to antigen.

5. The in vitro and/or ex vivo diagnostic method according to claim 4, wherein the biological sample is selected from the group consisting of in vitro hMPV-infected cells, nasal secretions, nasal washes, pharyngeal secretions and bronchial secretions or washings.

6. The in vitro and/or ex vivo diagnostic method according to claim 4, wherein a technique used for detecting antibody binding to antigen corresponds to ELISA, immunofluorescence, immunohistochemistry, immunochromatography, flow cytometry, cellsorter, immunoprecipitation and/or Western blotting.

7. The in vitro and/or ex vivo diagnostic method according to claim 4, wherein the antibody or fragment thereof is conjugated to a marker allowing its detection.

8. The in vitro and/or ex vivo diagnostic method according to claim 7, wherein the antibody is bound to a marker selected from the group consisting of fluorophores, biotin, radioisotopes, metals and enzymes.

9. A diagnostic kit for detecting hMPV, wherein the kit comprises the monoclonal antibody against hMPV according to claim 1.

10. The diagnostic kit according to claim 9, wherein the antibody is attached to a solid support.

11. The diagnostic kit according to claim 10, wherein the solid support is a membrane formed by one of the compounds selected from the group consisting of nitrocellulose, cellulose, polyethylene and nylon.

12. The diagnostic kit according to claim 9, wherein the kit further comprises components for performing an immunochromatographic test, luminex, flow cytometry, immunofluorescence, radioimmunoassay, Western blot, Dot plot, ELISA, immunodiffusion or immunoprecipitation.

* * * * *

SEQUENCE LISTING

<160> NUMBER OF SEQ ID NOS: 12

<210> SEQ ID NO 1
<211> LENGTH: 154
<212> TYPE: PRT
<213> ORGANISM: murine

<400> SEQUENCE: 1

Met Glu Cys Ser Trp Val Phe Leu Phe Leu Ala Ala Thr Ala Thr Gly
1               5                   10                  15

Val His Ser Gln Val Gln Pro Gln Gln Ser Gly Pro Glu Leu Val Arg
            20                  25                  30

Pro Gly Ala Ser Val Lys Met Ser Cys Lys Ala Ser Gly Tyr Thr Phe
        35                  40                  45

Thr Ser Ser Trp Met His Trp Val Lys Gln Arg Pro Gly Gln Gly Leu
    50                  55                  60

Glu Trp Ile Gly Met Ile Asp Pro Ser Asn Ser Glu Thr Arg Leu Asn
65                  70                  75                  80

Gln Lys Phe Lys Asp Lys Ala Thr Leu Asn Val Asp Lys Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Ile Arg Asp Trp Phe Ala Tyr Trp Gly Gln Gly Thr
        115                 120                 125

Leu Val Thr Val Ser Ala Ala Lys Thr Thr Pro Pro Ser Val Tyr Pro
    130                 135                 140

Leu Val Pro Gly Ser Leu Gly Ile Glu Phe
145                 150

<210> SEQ ID NO 2
<211> LENGTH: 47
<212> TYPE: PRT
<213> ORGANISM: murine

<400> SEQUENCE: 2

Met Glu Thr Asp Thr Leu Leu Leu Phe Ser Phe Phe His Ile Leu
1               5                   10                  15

Pro Leu Lys Cys Ser Phe Ser Ser Leu Ser Ser Ser Lys Ser Leu Leu
            20                  25                  30

Pro Ser Ser His His Pro Val Ser Leu Gly Ile Thr Ser Glu Phe
        35                  40                  45

<210> SEQ ID NO 3
<211> LENGTH: 462
<212> TYPE: DNA
<213> ORGANISM: murine

<400> SEQUENCE: 3
atggaatgca gctgggtctt cctcttcttg gcagcaacag ctacaggtgt ccactcccag      60
gtccaaccgc agcagtctgg gcctgagctg gtgaggcctg gggcttcagt gaagatgtcc     120
tgcaaggctt caggctatac cttcaccagc tcctggatgc actgggtgaa acagaggcct     180
ggacaaggcc ttgagtggat tggcatgatt gatccttcca atagtgaaac taggttaaat     240
cagaaattca aggacaaggc cacattgaat gtagacaaat cctccaacac agcctacatg     300
cagctcagca gcctgacatc tgaggactct gcagtctatt actgtgcaat aagggactgg     360
tttgcttact ggggccaagg gactctggtc actgtctctg cagccaaaac gacacccca      420

```
tccgtttatc ccttggtccc tgaaagcttg ggaatcgaat tc                   462
```

<210> SEQ ID NO 4
<211> LENGTH: 142
<212> TYPE: DNA
<213> ORGANISM: murine

<400> SEQUENCE: 4

```
atggagacag acacactcct gctatttcct ttcttctttc atatattacc tctcaagtgc   60
agtttctcct ccctctcctc ctctaagtcc cttcttccat cttcccacca tccagtaagc  120
ttgggaatca ctagtgaatt cg                                            142
```

<210> SEQ ID NO 5
<211> LENGTH: 156
<212> TYPE: PRT
<213> ORGANISM: murine

<400> SEQUENCE: 5

```
Met Glu Trp Ser Trp Leu Trp Val Leu Leu Trp Val Pro Gly Ser
1               5                   10                  15

Val Phe Leu Phe Leu Met Ala Val Val Thr Gly Val Asn Ser Glu Val
            20                  25                  30

Gln Leu Gln Gln Ser Gly Thr Glu Leu Val Lys Pro Gly Ala Ser Val
        35                  40                  45

Lys Leu Ser Cys Thr Ala Ser Gly Phe Asn Ile Thr Gln Ser Pro Ala
    50                  55                  60

Ser Leu Ala Val Ser Leu Gly Gln Arg Ala Thr Ile Ser Tyr Arg Ala
65                  70                  75                  80

Ser Lys Ser Val Ser Thr Ser Gly Tyr Ser Tyr Met His Trp Asn Gln
                85                  90                  95

Gln Lys Pro Gly Met Glu Trp Ser Trp Val Phe Leu Phe Leu Ala Ala
            100                 105                 110

Thr Ala Thr Gly Val His Ser Gln Val Gln Leu Gln Gln Ser Gly Pro
        115                 120                 125

Glu Leu Val Arg Pro Gly Ala Ser Val Val Thr Val Ser Ala Ala Lys
    130                 135                 140

Thr Thr Pro Pro Pro Val Tyr Ala Leu Gly Pro Trp
145                 150                 155
```

<210> SEQ ID NO 6
<211> LENGTH: 124
<212> TYPE: PRT
<213> ORGANISM: murine

<400> SEQUENCE: 6

```
Met Glu Ser Asp Thr Leu Leu Thr Gly Asp Ile Val Leu Thr Gln Ser
1               5                   10                  15

Pro Ala Ser Leu Ala Val Ser Leu Gly Gln Arg Ala Thr Ile Ser Tyr
            20                  25                  30

Arg Ala Ser Glu Gln Gly Leu Glu Trp Asp Pro Lys Phe Gln Gly Lys
        35                  40                  45

Ala Thr Ile Thr Ala Asp Thr Ser Asn Thr Ala Tyr Leu Gln Leu
    50                  55                  60

Ser Ser Leu Thr Ser Tyr Gln Gln Thr His Pro Thr Gln Pro Thr
65                  70                  75                  80

Cys Asn Ser Ala Ala Trp His Leu Arg Thr Leu Pro Ser Ile Thr Val
                85                  90                  95
```

Arg Ala Ala Ser Thr Cys Gly Leu Trp Thr Thr Gly Val Lys Glu Leu
            100                 105                 110

Tyr Ser Ser Ser Ile Phe Pro Pro Ser Ser Lys Leu
            115                 120

<210> SEQ ID NO 7
<211> LENGTH: 468
<212> TYPE: DNA
<213> ORGANISM: murine

<400> SEQUENCE: 7
atggaatgga gctggttatg ggtactgctg ctctgggttc caggttccgt cttcctcttc      60
ctgatggcag tggttacagg ggtcaattca gaggttcaac tgcagcagtc tgggacagaa     120
cttgtgaagc caggggcctc agtcaaattg tcctgcacag cttctggctt caacattaca    180
cagtctcctg cttccttagc tgtatctctg ggcagaggg ccaccatctc atacagggcc     240
agcaaaagtg tcagtacatc tggctatagt tatatgcact ggaaccaaca gaaaccagga    300
atggaatgga gctgggtctt cctcttcttg gcagcaacag ctacaggtgt ccactcccag    360
gtccaactgc agcagtctgg gcctgagctg gtgaggcctg ggcttcagt ggtcactgtc     420 tctgcagcca aaacaacacc cccacccgtc tatgcccttg gcccctgg                 468

<210> SEQ ID NO 8
<211> LENGTH: 372
<212> TYPE: DNA
<213> ORGANISM: murine

<400> SEQUENCE: 8
atggagtcag acacactgct gactggtgac attgtgctga cacagtctcc tgcttcctta     60
gctgtatctc tggggcagag ggccaccatc tcatacaggg ccagcgaaca gggcctggag    120
tgggacccga agttccaggg caaggccact ataacagcag acacatcctc aacacagcc     180 tacctgcaac tcagcagcct gacatcttac agcagacac atcctccaac acagcctacc    240
tgcaactcag cagcctggca tctgaggaca ctgccgtcta ttactgtgcg agcggcttct    300
acttgcggac tatggactac tggggtcaag gaactgtatt catcttccat cttcccacca    360
tccagtaagc tt                                                         372

<210> SEQ ID NO 9
<211> LENGTH: 33
<212> TYPE: DNA
<213> ORGANISM: murine

<400> SEQUENCE: 9
gggaattcat ggagacagac acactcctgc tat                                   33

<210> SEQ ID NO 10
<211> LENGTH: 39
<212> TYPE: DNA
<213> ORGANISM: murine

<400> SEQUENCE: 10
actagtcgac atggagwcag acacactsct gytatgggt                             39

<210> SEQ ID NO 11
<211> LENGTH: 33
<212> TYPE: DNA
<213> ORGANISM: murine

-continued

```
<400> SEQUENCE: 11
gggaattcat grasttskgg ytmarctkgr ttt                              33

<210> SEQ ID NO 12
<211> LENGTH: 35
<212> TYPE: DNA
<213> ORGANISM: murine

<400> SEQUENCE: 12
actagtcgac atgaacttyg ggytsagmtt grttt                            35
```